US00RE42231E

(19) United States
(12) Reissued Patent
Spurgeon

(10) Patent Number: US RE42,231 E
(45) Date of Reissued Patent: Mar. 22, 2011

(54) ADAPTABLE FILTER SAMPLING DEVICE

(76) Inventor: Joe C. Spurgeon, Fullerton, CA (US)

(21) Appl. No.: 11/207,206

(22) Filed: Aug. 18, 2005

Related U.S. Patent Documents

Reissue of:
(64) Patent No.: 6,779,411
Issued: Aug. 24, 2004
Appl. No.: 10/017,151
Filed: Dec. 14, 2001

(51) Int. Cl.
*G01N 1/00* (2006.01)

(52) U.S. Cl. ..... 73/863.23
(58) Field of Classification Search ..... 73/28.01, 73/28.04, 28.05, 28.06, 863.32, 863.33, 863.21–863.25, 73/865.5; 96/413; 916/413; 209/237, 403–405, 209/408
See application file for complete search history.

(56) References Cited

U.S. PATENT DOCUMENTS 3,966,439 A * 6/1976 Vennos ..... 73/963.22
3,983,743 A * 10/1976 Olin et al. ..... 73/28.06
4,155,247 A 5/1979 Kaczmarek et al.
4,426,214 A 1/1984 Vandrish
5,201,231 A 4/1993 Smith
5,304,125 A * 4/1994 Leith ..... 604/57
5,898,114 A 4/1999 Basch et al.
6,517,593 B1 2/2003 Robertson et al.
6,632,271 B2 10/2003 Robertson et al.
7,051,605 B2 * 5/2006 Lagraff et al. ..... 73/863.22
7,135,060 B2 * 11/2006 Jordan, Sr. et al. ..... 96/413

* cited by examiner

*Primary Examiner*—Robert R Raevis
(74) *Attorney, Agent, or Firm*—David G. Duckworth; Russo & Duckworth, LLP

(57) ABSTRACT

An adaptable filter sampling device is provided for localizing the utilized area of a filter medium. The filter sampling device of the present invention includes a filtration cassette having an inlet port, a body portion having an internal cavity, and an outlet port. Positioned within the body portion across the internal cavity is a filtration medium having a predetermined pore size for collecting particles. In addition, the filter sampling device includes an interchangeable restrictor plate made in various forms to enable its use with commercially available filter mediums and filtration cassettes. The restrictor plate includes one or more portals for directing the flow of gases or liquids through the filter sampling device. Preferably, the restrictor plate is positioned anterior and abutting the filter medium in relation to the particle exposure so that a gas or liquid is directed to a defined localized area of the filter medium. The localized area of filtration enables easier microscopic analysis of the filter medium and dramatically reduces the time required to collect and analyze a filtration sample. Moreover, the restrictor plates may have single or multiple portals. The portals may vary in size and shape or, in the case of multiple-restrictor plates, may be identical for replicate and duplicate sampling. Additionally, the portals may be specifically tailored to correspond with a particular microscope's focal views.

13 Claims, 5 Drawing Sheets

ADAPTABLE FILTER SAMPLING DEVICE

Matter enclosed in heavy brackets [ ] appears in the original patent but forms no part of this reissue specification; matter printed in italics indicates the additions made by reissue.

BACKGROUND OF THE INVENTION

The present invention relates to sampling devices for capturing airborne or liquid-suspended particles. More specifically, the present invention relates to an apparatus adapted to improve the collection efficiency of filtered particles.

There are numerous prior art filter sampling devices available today. For example, as shown in FIG. 1, a typical filter sampling device consists of a filtration cassette, a filter medium, and filter support pad. The filtration cassette typically has an inlet and outlet for directing the flow of an initial sample medium, either liquid or gas. Using a vacuum source, gas and/or liquid molecules, as well as particles, are made to pass through the filter medium. The filter medium selectively retains particles based on the particle's size.

An additional conventional air sampling device is commercially available under the trade name, Air-O-Cell™. This air sampler includes a two part cassette having a narrowing inlet and an outlet which is also connected to a vacuum source. Between the two parts of the cassette is an approximate slit directing the air flow onto a 2 mm×14 mm. impactor plate having an adhesive on the plate's upper side. In operation, spores, pollen, fibers, etc. enter through the inlet, strike the plate and are adhered to its surface. For analysis, the plate is removed and viewed under a microscope. Unfortunately, some particles carried by lower air flow rates are swept around the plate, causing a loss of sample; whereas particles carried by higher flow rates tend to be disrupted and/or bounced upon impacting the plate, making collection difficult.

Similar to the apparatus described above, European Patent No. 0,129,983 discloses a filter cassette for sampling airborne particles having an inlet, an outlet and a frustoconically shaped filter medium positioned in between.

U.S. Pat. No. 5,437,198 describes a device for separating and capturing airborne particles having a slit nozzle inlet and an internal porous impaction surface. Unimpacted particles follow the air flow past the impaction surface to be either later collected or discharged.

U.S. Pat. No. 4,764,186 describes an adhesive particle impactor for long-term sampling and separating of particles of a pre-determined size. The impactor assembly includes a housing having a plurality of elongate slots to direct heavy dust particles to impact the surface areas of the impactor plate while allowing the loss of some particles around the impactor plate.

U.S. Pat. No. 5,693,895 discloses an airborne particle impaction sampler wherein airborne particles are sucked into a narrowing inlet. An adhesive impactor plate is positioned approximately 1 mm from the inlet, allowing air to circulate around the impactor plate. This positioning is engineered so that particles as small as 2 μm are collected on the impactor plate while smaller particles are permitted to be swept past and eventually discharged.

U.S. Pat. No. 3,518,815 discloses an apparatus for converting a gas phase sample into a liquid phase sample. The device has a round rotating disk and a liquid feeder to provide a continuous liquid film to be maintained on the disk. In addition, a plurality of nozzles are positioned immediately upstream of the rotating collection disk to prevent the air flow from interrupting the integrity of a liquid substrate film maintained on the disk.

U.S. Pat No. 5,304,125 discloses an impactor assembly having a chamber, with an inlet and an outlet, and first and second impactor plates positioned in between. The first impactor plate has the same diameter as the inlet and has at least one slot positioned so as to permit a flow of gas to eventually either: impact the surface of a second impactor plate or be discharged through the outlet. The device is designed to remove large particles from a medicament aerosol prior to a patient's inhalation or application.

U.S. Pat. No. 3,957,469 describes a filter cassette having a removable capsule for measuring ambient airborne dust. An adhesive plate is positioned a distance from the inlet port where it collects airborne particles. Air flow continues to flow around the plate and through a flange that supports a tared capsule. While, dust particles collect on the capsule, the remaining air flow is exhausted through an outlet port. Measurement is taken by carefully weighing the capsule before and after being placed in the cassette, with the difference in weight providing the amount of dust trapped in the filter capsule.

Unfortunately, each of the above described filter sampling devices suffer from one or more disadvantages. Conventional filter samplers shown in FIG. 1 provide for almost 100% collection efficiency for particles greater than a predetermined size. This high efficiency is accomplished by the use of a permeable filtration medium having a predetermined pore size. However, the conventional filter samplers include a filtration medium so large that they are not advisable for use with microscopic analysis. For example, a standard filtration cassette having a filter medium 25 mm in diameter has a total surface area of 385 $mm^2$. To completely analyze the filter medium using a standard microscope equipped with a 100 × oil immersion objective, having a field of view of 0.024 $mm^2$, analysis of 16,042 fields of view would be required. Even analysis of 25% of these fields, a percentage considered sufficient by many skilled in the art, would require visual analysis of 4,011 fields of view, far too many for efficient study.

Meanwhile, the "impactor" filter sampling devices provide for much smaller sampling areas. For example, a typical Air-O-Cell™ sampler has an adhesive gel strip having dimensions of 2 mm×14.5 mm, providing a sampling area of 29 $mm^2$. Using the same microscope and applying a 25% analysis rate requires a relatively reasonable analysis of 235 fields of view. Unfortunately, impactor sampling devices permit particles to be swept past the impactor plate, and thus do not provide nearly 100% collection efficiency.

Thus, it would be advantageous to have a filter sampling device that provides for nearly 100% collection efficiency.

Furthermore, it would be advantageous that the filter sampling device provides for a sufficiently small sampling area suitable for efficient microscopic analysis.

It would also be advantageous if the filter sampling device were adaptable to provide for various sampling areas, utilizing a single filtration medium.

In addition, it would be advantageous if the filter sampling device provided for multiple sampling areas, utilizing a single filtration medium.

Thus, there is a need for a filter sampling device that provides solutions for the functional limitations described above. More specifically, the desired filter sampling device should be able to: (1) adaptively modify the area of filtration;

(2) effectively tailor the utilized area of a filter medium for viewing on a particular microscope; (3) simultaneously collect replicate or duplicate filter samples; and (4) achieve the foregoing without losing any amount of particle filtration.

BRIEF SUMMARY OF INVENTION

An adaptable filter sampling device is provided for localizing the utilized area of a filter medium. The localized area of filtration enables easier microscopic analysis of the filter medium and dramatically reduces the time required to collect and analyze a filtration sample. This adaptable filter sampling device can be applied to gas and liquid phase mediums.

To this end, the adaptable filter sampling device utilizes prior art technology found in filtration cassettes and filter mediums. In particular, the filter sampling device of the present invention includes a filtration cassette having an inlet port, a body portion having an internal cavity, and an outlet port. Positioned within the body portion across the internal cavity is a filtration medium having a predetermined pore size for collecting particles.

In addition, the filter sampling device includes an interchangeable restrictor plate having one or more portals for directing gas or fluid flow to one or more defined areas of the filter medium. The restrictor plate is interchangeable with commercially available cassettes and so may be used to modify other filtration cassettes. Preferably, the restrictor plate is positioned anterior and abutting the filter medium in relation to the particle exposure. This design ensures that essentially 100% of the medium initially sampled, whether gas or liquid, is filtered within a defined localized area of the filter medium. The restrictor plate may be made in various forms to enable its use with commercially available filter mediums and filtration cassettes. In addition, the restrictor plate may be incorporated into the body of the cassette, or the restrictor plate may stand alone as an adjunct to the body.

The restrictor plates may have single or multiple portals. Moreover, the portals may vary in size and shape, or in the case of multiple-portal restrictor plates, may include portals which are identical in shape for replicate and duplicate sampling. Additionally, portals may be specifically tailored to correspond with a particular microscope's focal views.

The filter sampling device of the present invention provides for nearly 100% collection efficiency. Collection efficiency is largely due to the positioning of the restrictor plate so that is abuts the filter medium.

Furthermore, the filter sampling device provides for sufficiently small sampling area to be suitable for efficient microscopic analysis. Reduced sampling area results in proportional increases in sensitivity and correspondingly decreases the time required for sampling.

The filter sampling device is also adaptable enabling one to use a single device providing various sampling areas without sacrificing a wide range of flow rates.

In addition, the filter sampling device provides for multiple sampling areas, for replicate or multiple analysis, while utilizing a single filtration medium.

Other features and advantages of the present invention will be appreciated by those skilled in the art upon reading the detailed description which follows with reference to the attached drawings.

DETAILED DESCRIPTION OF THE INVENTION

Figure 1:
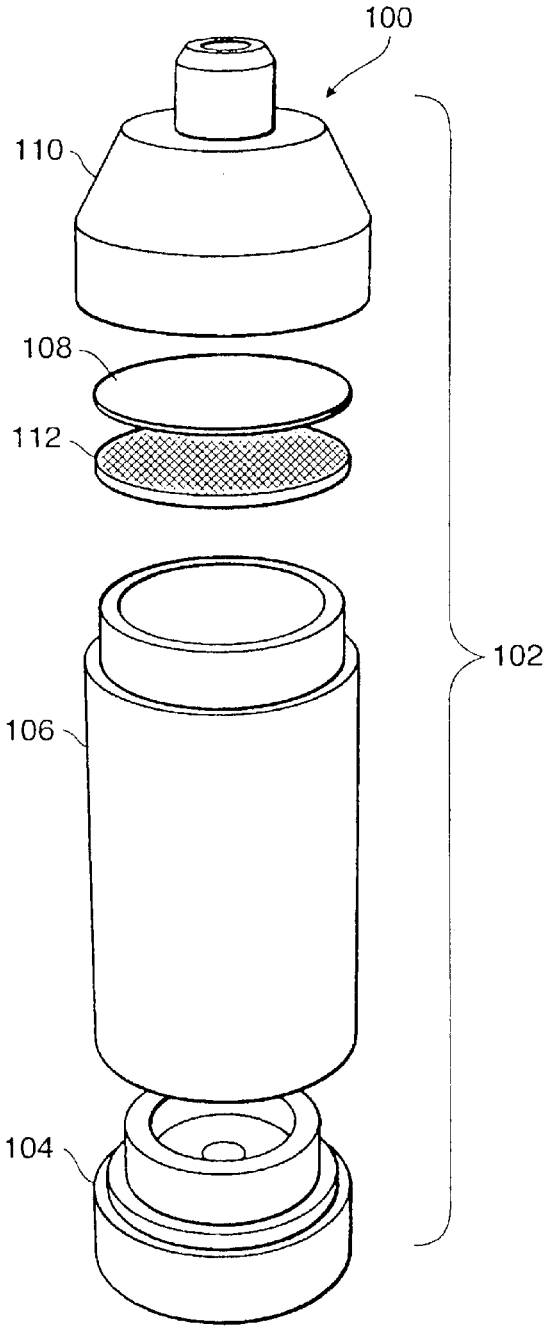
FIG. 1 (Prior Art)
FIG. 1 is an exploded side view of a filter sampling device found in the prior art.

While the present invention is susceptible of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

Figure 10:
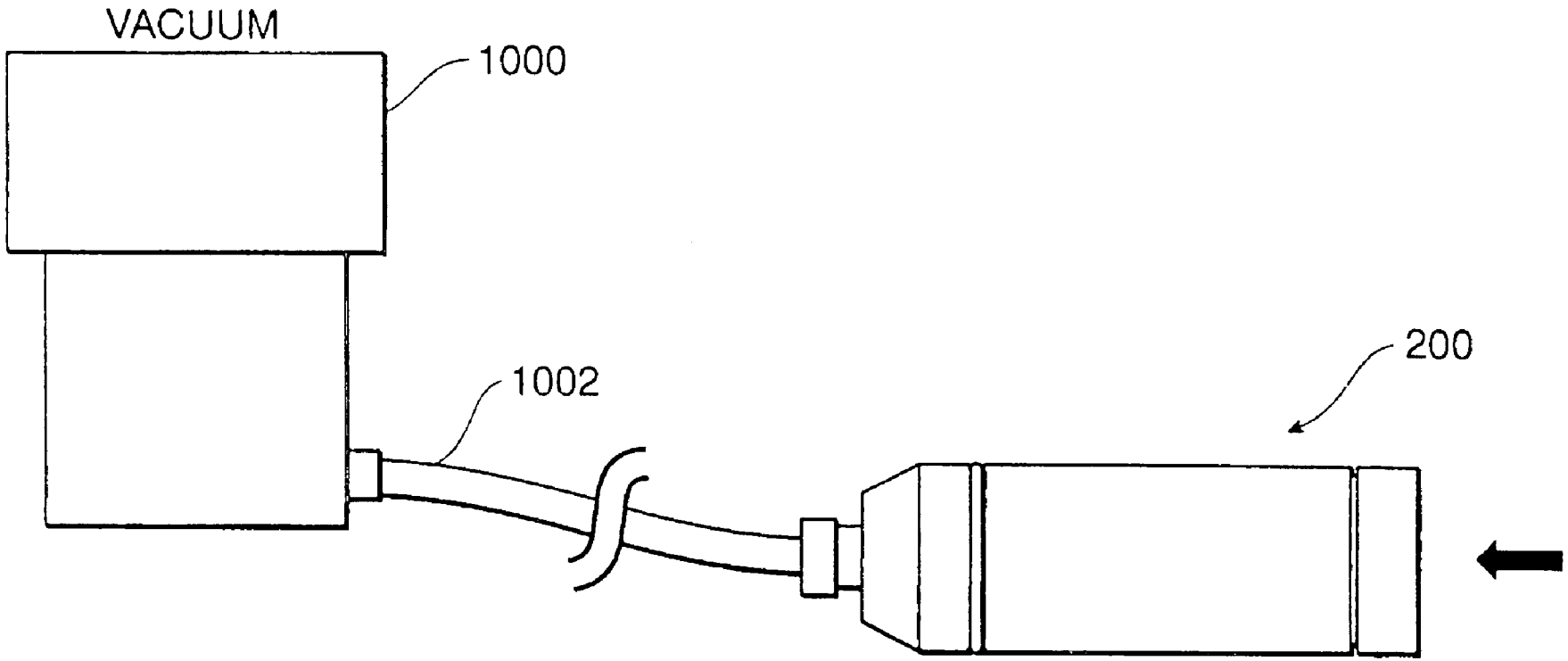
FIG. 10 is a side view of the adaptable air sampling device as used with a vacuum source.

FIG. 1 illustrates a conventional filter sampling device 100 including a filtration cassette 102 having an inlet port 104, a body portion 106, filter support pad 108, an outlet port 110, and a filter medium 112. Though not shown in the drawings, an O-ring may be provided in an assembled filtration cassette 102 to reduce the chance of leakage. In operation, and with reference to FIG. 10, a vacuum source is connected to the outlet port 110 to draw liquids or gases through the inlet port 104 and body portion 106 of the sampling device to be expelled through the outlet port.

As shown in FIGS. 2–7, the adaptable filter sampling device 200 of the present invention includes a filtration cassette 102 having an inlet port 104, a body portion 106, filter support pad 108, outlet port 110, and a filter medium 112. The filter medium 112 used in the adaptable filtration cassette 200 may vary in size and shape. Common filter mediums 112 with diameters of 10 mm, 16 mm, 37 mm, 47 mm, as well as, the standard 25 mm filter, are commercially available. Commercial vendors for these types of filter mediums 112 are well known to one skilled in the art.

Of importance, the adaptable filter sampling device 200 also includes an interchangeable restrictor plate 202 for adapting the conventional filter sampling device. Preferably, the restrictor plate 202 is positioned anterior to and abutting the filter medium 112 and includes one or more portals 204 for directing particulate flow to a defined area of the filter medium. The collection efficiency is significantly enhanced by abutting the filter medium 112 and restrictor plate 202, as opposed to having some distance between collection mechanism and air flow entry, as can be found in the prior art.

Figure 2:
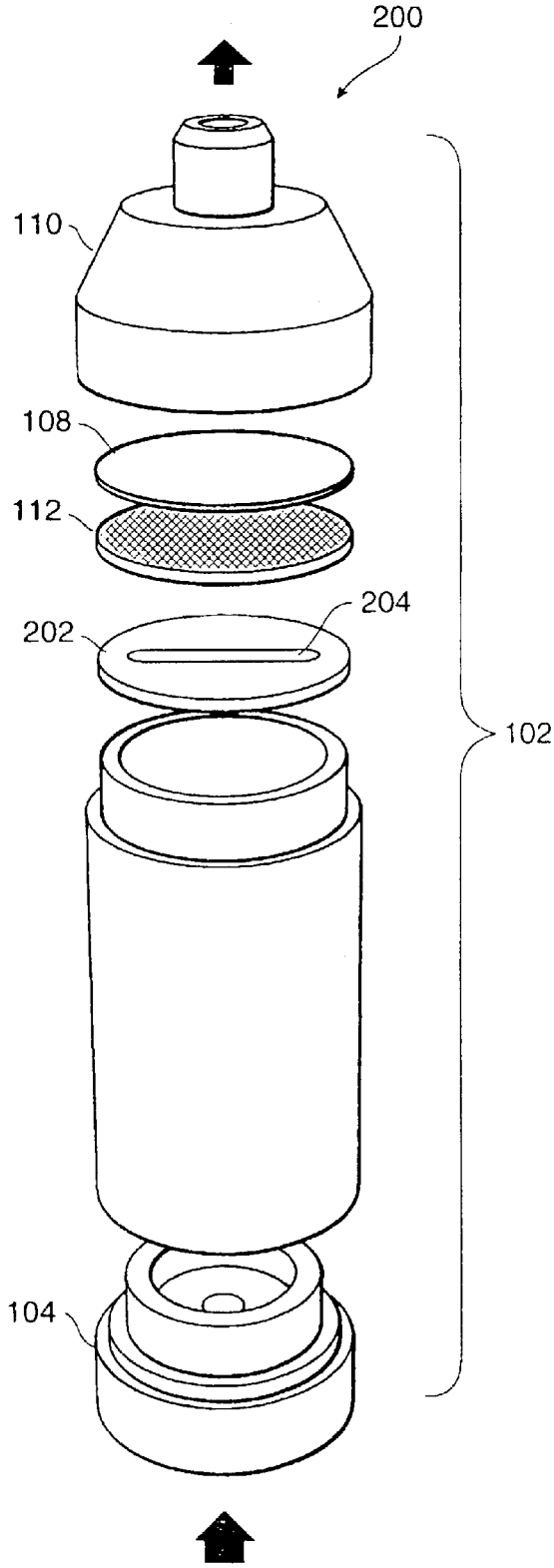
FIG. 2 is an exploded side view of the adaptable filter sampling device, illustrating the restrictor plate positioned directly anterior to the filter medium in relation to the particle exposure.

The preferred embodiment of the restrictor plate 202 is as an optional fitting which is positioned within a conventional filtration cassette 102, shown in FIG. 1. The restrictor plate 202 is interchangeable with commercially available air filtration cassettes 102, therefore freely modifying standard filtration cassettes 102. As shown in FIG. 2, the restrictor plate 202 is constructed as a plate, or disk-like barrier, having a portal 204 for allowing particles to pass through a localized area of the plate to strike the filter medium in a defined area. The restrictor plate 202 of this embodiment may be removed or interchanged with another restrictor plate 202 without impairing the functionality of the filtration cassette 102. The restrictor plate 202, as well as the portal 204, may be any geometric shape and need not be similar to each other. For example, either may be circular, square, rectangular, octagonal, etc, and their respective shapes are entirely independent of each other. Moreover, the portal 204, providing a means for particle penetration or access to the filter medium 112, may be an opening, conduit, cutout, slit, hole, or any type of similar construction for use in conjunction with a permeable membrane.

Figure 3:
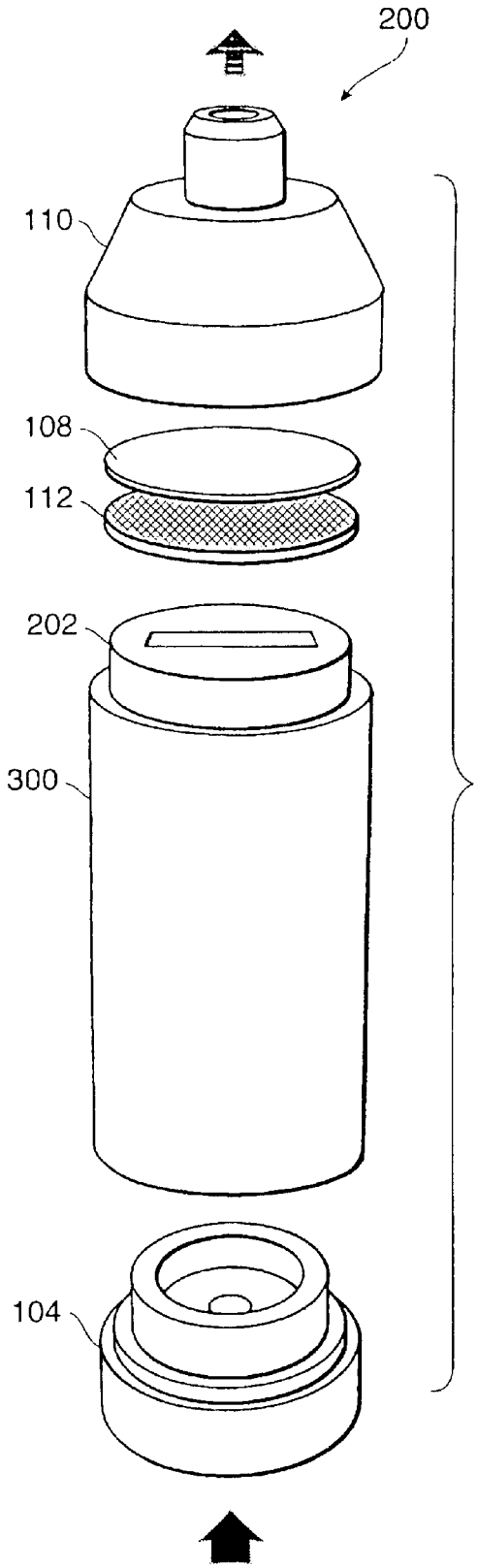
FIG. 3 is an exploded side view of a second embodiment of the adaptable air sampling device demonstrating the restrictor plate incorporated into a cassette fitting and positioned directly anterior to the filter medium in relation to the particle exposure.
Figure 4:
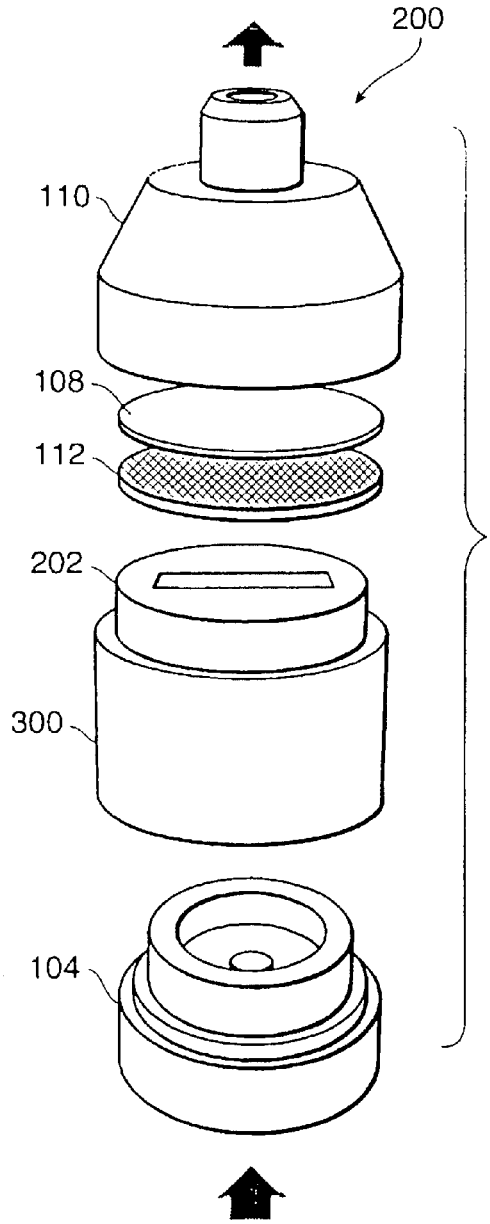
FIG. 4 is an exploded side view of a third embodiment of the adaptable air sampling device demonstrating the restrictor plate incorporated into a shortened cassette fitting and positioned directly anterior to the filter medium in relation to the particle exposure.

As shown in FIGS. 3 and 4, in additional preferred embodiments of the invention, the restrictor plate 202 and portal 204 are integrated into the body portion 300 of the cassette. The body portion 300 is interchangeable and permits substitution of other body portions having different dimensions. For example, FIG. 3 illustrates a filter sampling device 200 having an elongate body portion 300 which is ideally suited for wall sampling. Meanwhile, FIG. 4 illustrates a filter sampling device 200 having a truncated body portion 300 which is ideally suited for atmospheric sampling. Moreover, the ability to substitute body portions 300 permits the substitution of restrictor plates 202 having portals 204 of different numbers, sizes and/or configurations.

Figure 5:
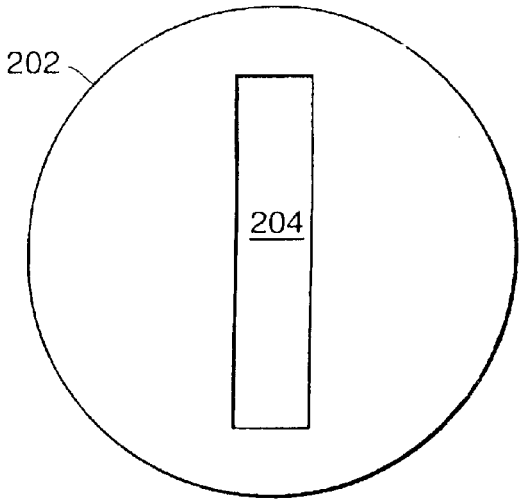
FIG. 5 is a top view of a restrictor plate with one portal.
Figure 6:
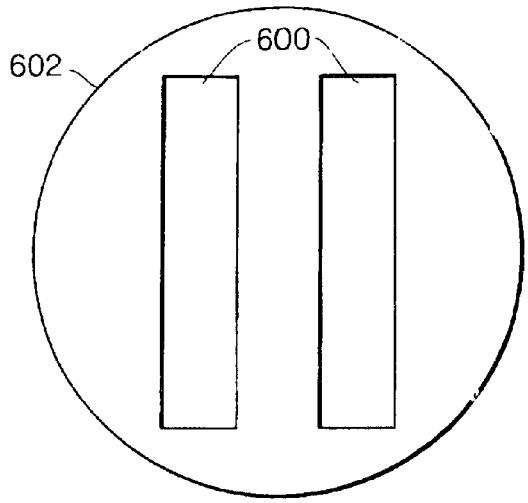
FIG. 6 is a top view of a restrictor plate with two portals.
Figure 7:
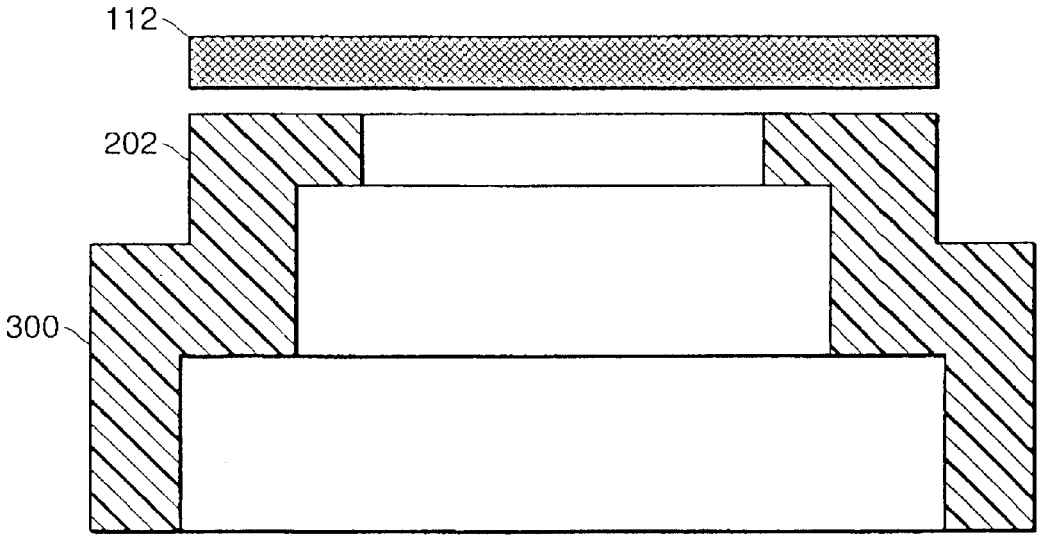
FIG. 7 is a cross section view illustrating the restrictor plate incorporated into a cassette fitting with the filter medium positioned directly posterior to the restrictor plate.

As shown in FIGS. 5 and 6, the restrictor plate 202 may include one or more portals 202, with the number of portals limited only by their size and the area of the filter medium. A multiple-portal restrictor plate 602 allows multiple samples, i.e. replicates or duplicates, to be collected simultaneously on one filter. These replicates may then be used for various purposes such as multiple method analysis or, in the case of duplicate analysis, to increase statistical confidence. One who is skilled in the art may determine other purposes and advantages to collecting replicate or duplicate samples simultaneously.

Figure 8:
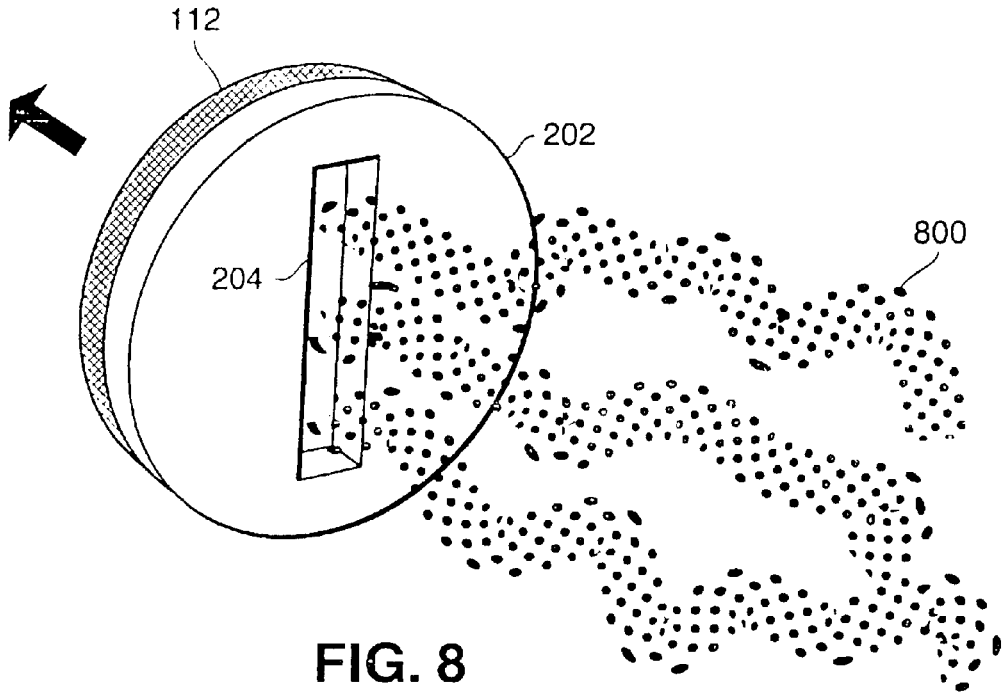
FIG. 8 is a perspective view demonstrating the pathway of airborne particles as they follow the air flow through the portal and are captured by the filter medium.

With reference to FIGS. 2–4 and 7–9, preferably, the restrictor plate 202 abuts the filter medium 112, sandwiching the filter medium 112 between the restrictor plate 202 and support pad 108. As shown in FIG. 8, the restrictor plate 202 is positioned anterior to and abutting the fillter medium 112 in relationship to the particle exposure flow 800. In operation, the restrictor plate 202 effectively limits the area that particles may pass through the filter medium, concentrating the sample into a localized area defined by portal 204, a substantially lesser area than the original filter size. Filtered air and particles too small to be captured by the filter medium 112 pass through the filter medium 112 and through the filtration cassette 102 to eventually be discharged through the outlet port 110.

In one preferred embodiment of the invention, the portal 204 comprises 6% of the total area of the filter medium 112. This arrangement allows a 15-fold increase in sensitivity or a 15-fold reduction in sampling time when compared to the entire area of a filter medium 112.

Figure 9:
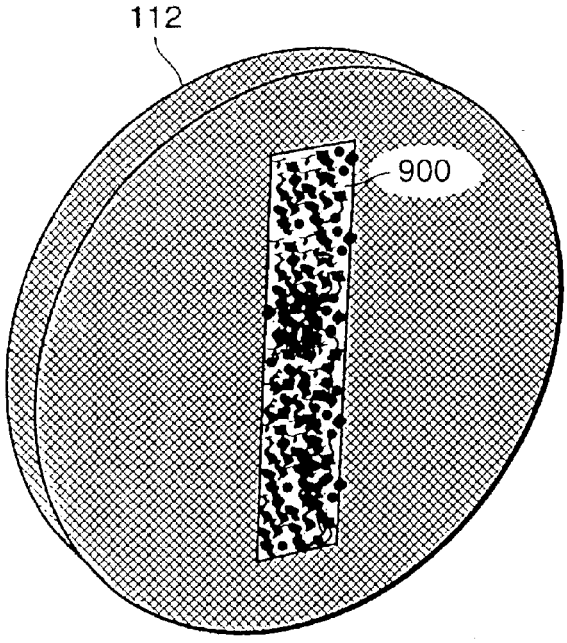
FIG. 9 is a perspective view of the filter medium after it has been positioned posterior to the restrictor plate in relation to the particle exposure and used to capture particles.

FIG. 9 depicts a filter medium 112 after it has been used in conjunction with a restrictor plate 202. The passage of particles to a localized area of impact 900 occurs only incident to where the portal 204 was positioned. Once the filter medium 112 and the particulates captured by the filter medium 112 are removed from the filter cassette 200, the particulates are ready to be analyzed, by microscopic or other methods of analysis.

The restrictor plate 202 supports the filter medium 112 and enables a wide range of acceptable flow rates. Once modified to incorporate a restrictor plate 202, the typical range of air flow rates is from less than one liter to over 15 liters per minute. Like the conventional filter apparatus illustrated in FIG. 1, the adaptable filter apparatus provides for 100% collection of particulates greater than a predetermined size independent of air flow rate, and over a wide range of air flow rates.

The size and the diameter of the cassette can reasonably vary. Optimal size of the cassette will largely depend on the types and selection of filter media available for that size cassette. Variations in cassette size can influence the appropriate sized filter medium 112, as well as, restrictor plate 202. Factors for determining an optimal filtration cassette 102 size will be readily determined by one skilled in the art and will not require undue experimentation.

Likewise, the dimensions of the portal 204 and corresponding particle impact area 900 may also vary as can be determined by those skilled in the art. Preferably, the portal's 204 dimensions create a narrow rectangular track, such as 1.6 mm×15 mm, 2 mm×14 mm, 2 mm×10 mm, 2.4 mm×10 mm, or 3 mm×10 mm, which are desirable to permit microscopic analysis performed in one direction and eliminate the need for multidirectional traverses. However, other dimensions and areas may be more desirable depending on the target particulate and the method of analysis. While the dimensions of the portal 204 in the plate may vary, a preferred embodiment is a portal 204 large enough to avoid destructive back pressure upon the filter medium 112, while remaining small enough to facilitate microscopic analysis.

Analysis of the filter medium 112 may vary. For example, following collection of the sample, the entire adaptable filter sampling device 200, or the filter medium 112 alone, may be sealed and shipped to a laboratory for analysis. Laboratory personnel can divide the filter using a surgical scalpel and utilize portions of the localized area of impact 900 for different purposes, such as microscopic analysis, chemical analysis, or culturing.

While certain materials, dimensions and arrangements have been described in detail as part of the preferred embodiments, those can be varied, where suitable, with similar results. For example, materials of the filtration cassette's 102 construction may be plastic, metal, or ceramic. Similarly, the restrictor plate 202 may be constructed of any gas and fluid impermeable material such as, but not limited to, plastic, metal, or ceramic. The filter medium 112 may be comprised of any number of suitable filtering materials. The following materials are provided as examples: mixed cellulose ester, polycarbonate, or glass filter.

The adaptable filter sampling device 200 is highly suitable for collecting most environmental contaminants that are typically collected on filter media. Asbestos and other types of fibers; lead-based paint particulate; heavy metals; bacteria; pollen; and fungi are examples of target particulate. As would be understood and can be determined by those skilled in the art without undo experimentation, other applications and target particulates are intended to be included within the embodiment of this invention.

Although the present invention has been described with reference to the preferred embodiments, workers skilled in the art will recognize that changes may be made in form and detail without departing from the spirit and scope of the invention. Having identified the present preferred embodiments thereof.

I claim:

1. An adaptable filtration cassette for collecting particulates in liquid or gas comprising:

a housing having a central conduit, an inlet port, and an outlet port;

a substantially planar filtration medium positioned within said housing substantially adjacent to said outlet port; and a removable substantially planar restrictor plate having a portal for localizing the utilized area of said filtration medium, said planar restrictor plate and said filtration medium positioned to abut one another for localizing the utilized area of said filtration medium;

said adaptable filter cassette operating in a first [and] *or* second mode, said first mode utilizes substantially all of the surface area of [the filter] *said filtration* medium; and said second mode incorporates said restrictor plate to localize particles to a portion of the [filter] *filtration* medium.

2. The adaptable filtration apparatus of claim 1 wherein the restrictor plate is incorporated into the [body] *housing* of the filtration cassette.

3. The adaptable filtration apparatus of claim 1 wherein the restrictor plate includes more than one portal.

4. The adaptable filtration apparatus of claim 1 wherein the restrictor plate includes two portals, each of said two portals being substantially rectangular and having dimensions between 1–5 mm×10–20 mm.

5. The adaptable filtration apparatus of claim 1 wherein said portal is substantially rectangular and has dimensions between 1–5 mm×10–20 mm.

6. A method for collecting particulates in liquid or gas comprising the steps of:

providing an adaptable filtration cassette for collecting particulates in liquid or gas including housing having a central conduit, an inlet port, and an outlet port; a substantially planar filtration medium positioned within the housing substantially adjacent to the outlet port; and a removable substantially planar restrictor plate having a portal for localizing the utilized area of the filtration medium, the planar restrictor plate and the *planar* filtration medium capable of being positioned to abut one another for localizing the utilized area of [a filter] *the filtration* medium;

collecting particulates in a first mode by filtering a gas or liquid through the [filter] *filtration* medium without said planar restrictor plate being positioned within said housing; and collecting particulates in a second mode by positioning the restrictor plate so that it abuts and is anterior to [a filter] *the filtration* medium in relation to particle exposure to direct particles to a localized area of the [filter] *filtration* medium and filtering a gas or liquid through the [filter] *filtration* medium.

7. The method for collecting particulates in liquid or gas of claim 6 wherein the [filter] *filtration* medium is substantially round and the restrictor plate's portal is substantially rectangular.

8. The method for collecting particulates in liquid or gas of claim 6 wherein the [filter] *filtration* medium is substantially round and has a diameter between 10 mm and 47 mm and the restrictor plate's portal is substantially rectangular and has dimensions between 1–5 mm×10–20 mm.

9. The method for collecting particulates in liquid or gas of claim 6 wherein the restrictor plate includes more than one portal.

10. The method for collecting particulates in liquid or gas of claim 9 wherein the restrictor plate includes two portals, each of said two portals being substantially and having dimensions between 1–5 mm×10–20 mm.

*11. A particulate sampling cassette for simultaneously collecting a plurality of particulate samples in gaseous environments comprising:*

*a housing having a central cavity, an inlet and an outlet for connection to a vacuum source;*

*a filtration sampling collection medium having a predetermined pore size positioned within said housing between said inlet and said outlet; and*

*a flow restrictor positioned within said housing including a plurality of portals for localizing the utilized area of said filtration sampling collection medium, said flow restrictor and said filtration sampling collection medium positioned adjacent and substantially engaging one another for reducing and localizing the utilized area of said filtration sampling collection medium to produce a plurality of discrete samples corresponding in number to the number of portals within said flow restrictor.*

*12. The particulate sampling cassette of claim 11 wherein the flow restrictor includes only two portals.*

*13. A method for collecting particulates in gaseous environments comprising the steps of:*

*providing a particulate sampling cassette including a housing having a central cavity, an inlet and an outlet for connection to a vacuum source, the cassette further having a filtration sampling collection medium having a predetermined pore size positioned within said housing between said inlet and said outlet, and a flow restrictor positioned within said housing including a plurality of portals for localizing the utilized area of the filtration sampling collection medium, the flow restrictor and the filtration sampling collection medium positioned adjacent and substantially engaging one another for reducing and localizing the utilized area of the filtration sampling collection medium to produce a plurality of discrete samples corresponding in number to the number of portals within the flow restrictor;*

*connecting said outlet to a vacuum source;*

*simultaneously collecting a plurality of particulate discrete samples corresponding in number to the number of portals within the flow restrictor by filtering a gas or liquid through the flow restrictor and filtration sampling collection medium.*

* * * * *